United States Patent [19]

Brown et al.

[11] Patent Number: 4,464,568
[45] Date of Patent: Aug. 7, 1984

[54] APPARATUS FOR DETECTION AND ANALYSIS OF URANIUM ORES

[75] Inventors: Graydon L. Brown; Larry L. Newlin, both of Ponca City, Okla.

[73] Assignee: Conoco Inc., Ponca City, Okla.

[21] Appl. No.: 226,361

[22] Filed: Jan. 19, 1981

[51] Int. Cl.³ .................................................. G01V 9/00
[52] U.S. Cl. .................................... 250/253; 250/461.1
[58] Field of Search ............... 250/461.1, 253, 255, 250/372, 302

[56] References Cited

U.S. PATENT DOCUMENTS 3,284,616 11/1966 Ernyei et al. ................ 307/220 R
4,236,071 11/1980 Chimenti ............................ 250/253
4,239,964 12/1980 Robbins et al. ................ 250/461.1

Primary Examiner—Alfred E. Smith
Assistant Examiner—Carolyn E. Fields
Attorney, Agent, or Firm—William J. Miller

[57] ABSTRACT

Apparatus for detection and analysis of secondary uranium ores to provide signature indication of type by ultraviolet induced fluorescence and detection of fluorescence excitation time, peak value and decay time. The apparatus employs laser irradiation of selected terrain and telescopic detection at specific light wavelengths, viz. the yellow to green band; and thereafter detected signals are processed with specific circuitry to obtain and provide readout of the signature parameters.

9 Claims, 4 Drawing Figures

APPARATUS FOR DETECTION AND ANALYSIS OF URANIUM ORES

BACKGROUND OF THE INVENTION

1. Field of the Invention

The invention relates generally to a system for uranium ore detection and, more particularly, but not by way of limitation, it relates to improved apparatus utilizing fluorescence for detection of uranium ores.

2. Description of the Prior Art

The prior art includes various forms of fluorescence detection systems that function primarily by irradiating a land or water mass with ultraviolet light for subsequent telescopic detection of the fluorescence thereby to ascertain the presence of certain substances. U.S. Pat. No. 3,736,428 in the name of Monroe discloses one form of airborne system wherein ultraviolet light is used for irradiation and an optical analyzer detects fluorescence for subsequent color separation and data output for identification of specific minerals. Yet another form of air surveillance sensing system utilizing ultraviolet light as disclosed in U.S. Pat. No. 3,961,187 in the name of Barringer, and this is a broad band system primarily directed to sea surveillance. The system provides detection but includes no specific means for analysis of the detected fluorescent response. Other patents of interest are U.S. Pat. Nos. 3,899,213 and 3,043,908, which teach the general surveillance system approach utilizing ultraviolet light with subsequent fluorescence detection as an indicator.

SUMMARY OF THE INVENTION

The present invention relates to improvements in mineral detection utilizing ultraviolet light fluorescence, which improvements are largely directed to analysis apparatus capable of providing specific output signature data for identifying particular forms of uranium ore. The system utilizes ultraviolet light irradiation with detection of subsequent fluorescence, either from an airborne position or a more localized land position, and any detected fluorescence is analyzed to provide an output indication of fluorescence peak intensity, fluorescence excitation rise time, and fluorescence decay time. The invention utilizes a laser transmitter with telescopic photo detection of fluorescence whereupon electrical signal output is filtered and applied to a sample and hold circuit that outputs a peak detection value for display indication. Pulse circuitry actuated in response to the differentiated fluorescence response signal then provides additional indication of the fluorescence response excitation rise time as well as the response decay time, each of which may be suitably displayed and/or recorded.

Therefore, it is an object of the present invention to provide a mineral direction system utilizing fluorescence that not only detects but provides specific signature data relative to each characteristic fluorescent response.

It is also an object of the present invention to provide an improved fluorescence analysis circuit having maximum response band width.

It is still further an object of the present invention to provide a system for detecting presence and amounts of specific uranium oxide ores.

Finally, it is an object of the present invention to provide a fluorescence detection system which may be utilized not only in airborne surveillance applications but also in land borne examinations directed to deposits and outcroppings of more specific location.

Other objects and advantages of the invention will be evident from the following detailed description when read in conjunction with the accompanying drawings which illustrate the invention.

DETAILED DESCRIPTION OF THE INVENTION

Figure 1:
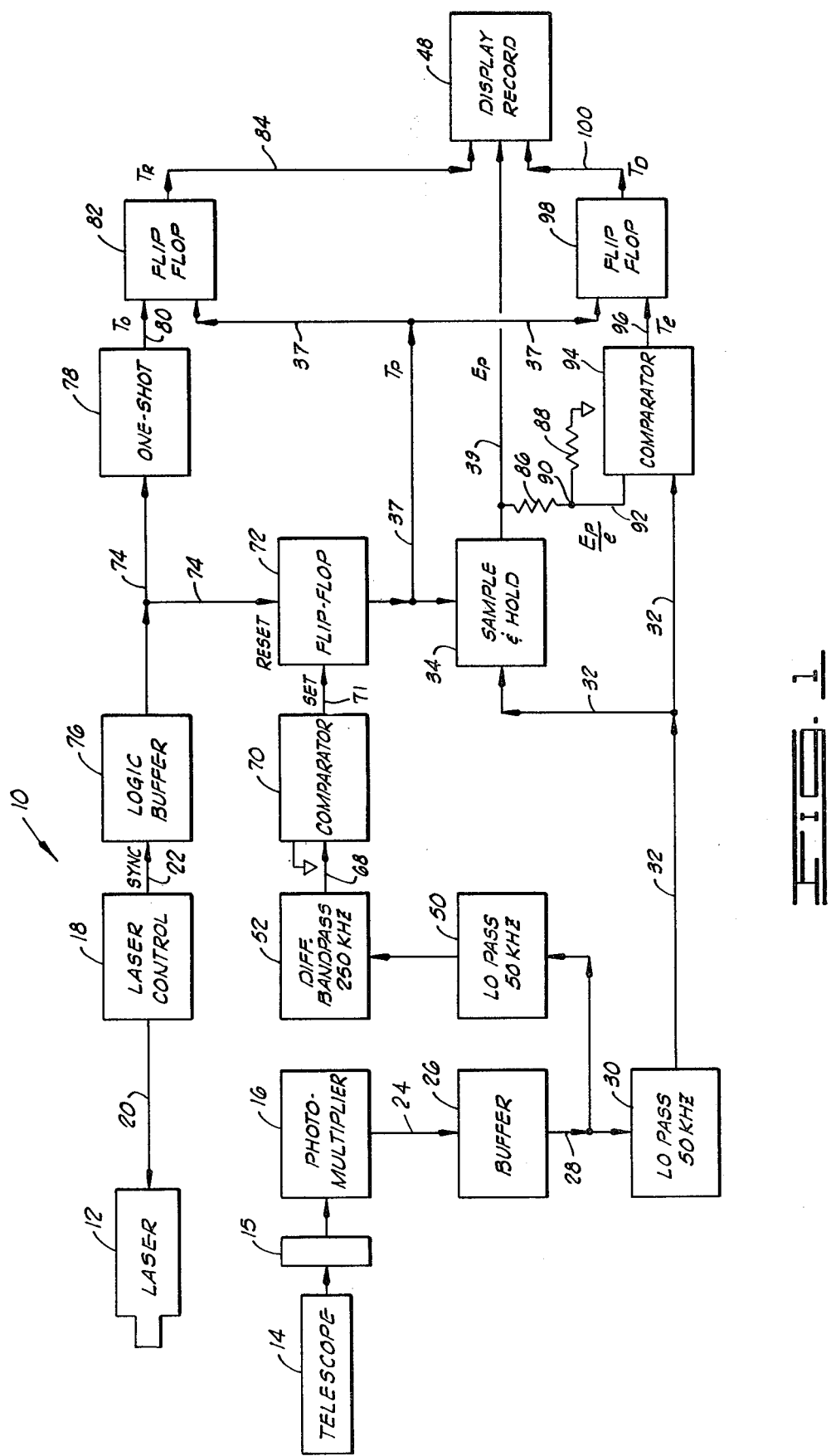
FIG. 1 is a block diagram of the present invention.

Referring to FIG. 1, the detection system 10 consists of a laser 12 for directing ultraviolet light on or along specific terrain, any fluorescence from which will be received by a telescope 14 and filter 15 for conversion to electrical energy in a photomultiplier 16. Such basic transmission and detection equipment is well known in the art as is documented by the prior art patents referred to hereinabove. In particular, however, the present system operates with laser 12 generating light output in the near ultraviolet at 337 nanometers wavelength. Fluorescent return from the desired uranium oxides is then approximately 520 nanometers, or within a preferred range of 500 nanometers to 550 nanometers (yellowish-green fluorescence), and fluorescent return within this range encompasses nearly all of the secondary uranium ores, i.e., uranium oxides, as well as some primary ores.

The laser 12 may be any commercially available portable-type laser operated in pulsed mode. In present design a nitrogen laser has been utilized as pulsed by laser control 18 at a maximum repetition frequency of 100 hertz or 10 milliseconds between pulses. The laser control 18 is conventional circuitry and provides the system clock with pulse repetition rate output on line 20, and data processing sync control is output via line 22. As stated, the laser energy output is tuned to the 337 nanometer wavelength and any fluorescent return detected within the field of view of telescope 14 is transmitted through a narrow band filter 15 to the photomultiplier 16. The narrow band filter 15, of well-known type, is selected to pass light in the range of 500 nanometers to 550 nanometers or a yellowish-green fluorescence. Any detected fluorescence is then converted in photomultiplier 16 to provide an electrical output signal on line 24 to a buffer stage 26. The buffer 26 is mounted in the photomultiplier tube housing and is primarily intended to provide a high impedance load for the photomultiplier 16 while also providing a low source impedance capable of driving a coaxial cable if used at line 28 for connection to the rest of the detector system. Buffer stage 26 may also provide voltage gain if this is found to be desirable.

Figure 2:
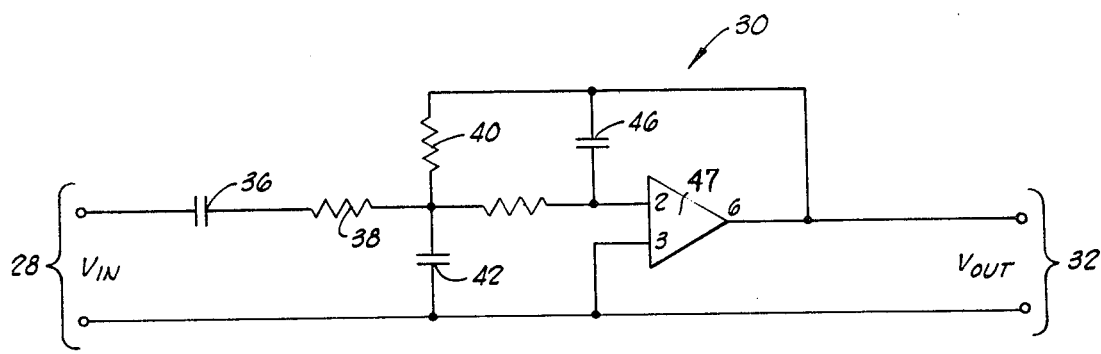
FIG. 2 is a schematic diagram of a low pass filter as may be utilized in the present invention.

Detector output signal on line 28 is applied to a low pass filter 30 having a 50 kilohertz upper limit whereupon the filtered output is applied by line 32 to a sample and hold circuit 34. A suitable form of low pass filter 30 is shown in FIG. 2, an active filter circuit utilizing an integrated circuit type LM-318. The active filter interconnection includes amplifier 47 and is as shown with component values as follows:
   Capacitor 36—0.33 microfarads
   Resistor 38—5.6 Kohms
   Resistor 40—22 Kohms
   Capacitor 42—1,000 picofarads
   Capacitor 46—100 picofarads The sample and hold stage 34 may be such as integrated circuit type LH-0043. Sample and hold circuit 34 is connected to hold a peak negative value signal by input of a peak time or $T_p$ pulse on line 37, and output from the sample and hold circuit 34 is available on lead 39 as the $E_P$ or peak value voltage for subsequent input to a display/recorder 48.

Figure 3:
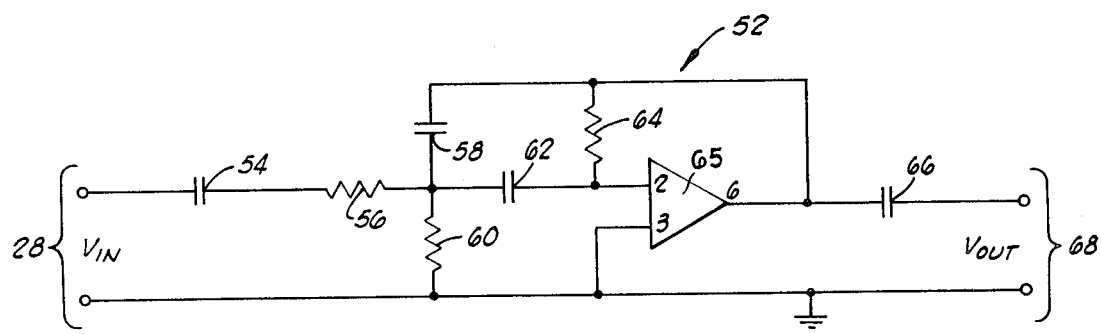
FIG. 3 is a schematic diagram of a differentiation band pass filter which may be utilized in the present invention.

Referring again to buffer stage 26, output detector signal on line 28 is also applied in parallel to a low pass filter 50, a filter of similar but not necessarily identical design to filter 30 as shown also in FIG. 2. The output from low pass filter 50 is then applied to a differentiator 52 which is band pass limited to 250 kilohertz. The differentiator 52 includes amplifier 65 and may be such as an integrated circuit type 318 and is shown in greater detail in FIG. 3 wherein component values are as follows:
   Capacitor 54—0.33 microfarads
   Resistor 56—2.63 Kohms
   Capacitor 58—30 picofarads
   Resistor 60—3 Kohms
   Capacitor 62—30 picofarads
   Resistor 64—21 Kohms
   Capacitor 66—30 microfarads Output from differentiator 52 is then applied on line 68 to input on a line 71 of comparator 70, a comparison input pin No. 2 being grounded. The comparator 70 may be such as integrated circuit type LM-311 and interconnected as shown. Output from comparator 70 is then available on a line 71 as SET output for input to a flip flop 72, a standard integrated circuit type 7474. Flip flop 72 receives SET input from line 71 and RESET input on lead 74 as it is output from a logic buffer 76 under control of sync pulse on line 22 from laser control 18. The sync pulse on line 22 is utilized for timing of the detector system by resetting flip flop 72 and triggering a one shot multivibrator 78. The timing of one shot 78 is adjustably preset in order to correct for accumulated delays between sync output and actual ultraviolet light output from laser 12, plus any anticipated travel time for light as calculated at 984 feet per microsecond in air. Hence, the one shot 78 should be set to time out at the time the ultraviolet light from the laser 12 would be reflected to the photomultiplier tube 16 and prior to any fluorescence excitation rise time, as will be further described. Thus, output on line 80 from one shot 78 is the time zero or $T_0$ pulse as input to flip flop 82.

Flip flop 82 receives input of the time zero, $T_0$ pulse on line 80 and reverse conduction on input of the peak time pulse $T_P$ as input on line 37, thereby to generate an output voltage pulse having a duration $T_R$ indicative of excitation rise time of the fluorescence. The $T_R$ pulse may also then be adapted for indication, recording, or display as shown generally by display/recorder 48. The display 48 may be any of the usual data recorders many of which are well-known in the geophysical and related arts.

Finally, a voltage divider consisting of series-connected resistors 86 and 88 is connected between the $E_P$ or peak voltage lead 39 and ground, resistors 86 and 88 being proportioned so that voltage tapped off at junction 90 is divided at a rate $E_P/e$ which equals 0.368 $E_P$ where e is the base of natural logarithms; and the tapped voltage is applied via line 92 to one input of a comparator 94, an integrated circuit type LM-311. The remaining input of comparator 94 receives input of the filtered detector output signal on line 32.

The voltage applied on line 92 is a constant proportion of the peak voltage $E_P$ as necessary to define an exponential decay in a period of one time constant. Thus, $$\frac{E_P}{e} = \frac{E_P}{2.718} = .368\, E_P$$

Figure 4:
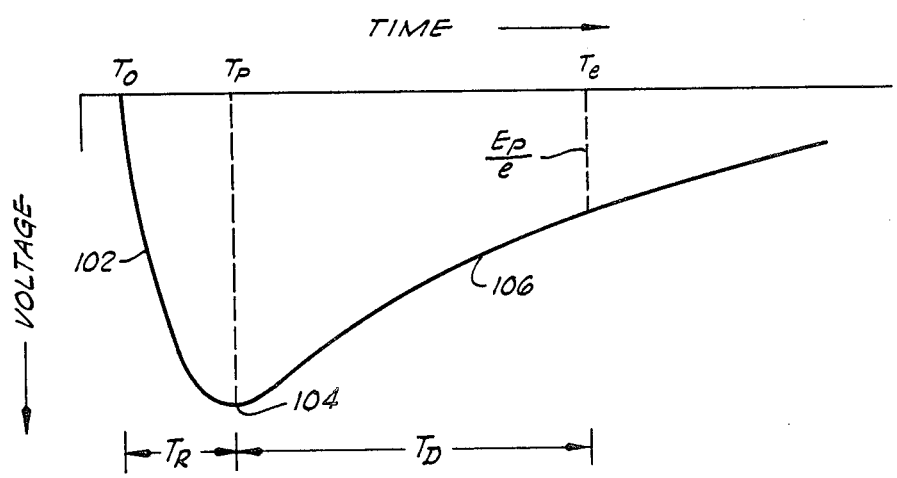
FIG. 4 is a graph representation of a specific mineral fluorescence response from initiation through decay time.

At time $T_e$ the fluorescence pulse on line 32 has decayed to be equal to the voltage on line 92, and under this condition the comparator 94 generates an output voltage on line 96 for input to flip flop 98 thereby terminating the time period $T_D = T_e - T_P$. Thus, the output from flip flop 98 is a voltage pulse having a duration which is indicative of the fluorescence decay time for the particular mineral being viewed, and the output pulse $T_D$ is applied on lead 100 to the display or record 48. FIG. 4 illustrates in graphic form a characteristic signature for a particular uranium oxide, viz. Autunite. Thus, for this particular uranium ore, fluorescence detection commences at time $T_0$ with a sharp rise time through the curve portion 102 to the peak 104 or time $T_P$ the time lapse or excitation rise time $T_R$ in this case is 12 microseconds. After the peak 104 the fluorescence decays through a curve portion 106 or decay time $T_D$, measurement being cutoff at the standard proportion $E_P/e$.

Nearly all oxides of uranium and some primary uranium ores provide some fluorescence in the particular response band width utilized, and each will exhibit characteristic signature upon readout of rise time, peak value and decay time. Those minerals exhibiting reliable response in order of their relative intensity are as follows:

| Relative Intensity | Mineral |
| --- | --- |
| Strong | Abernathyite, Andersonite, Autunite, Calcurmolite, Heinrichite, Liebigite, Metaheinrichite, Metauranospinite, Pseudo-autunite, Sabugalite, Saleeite, Schroeckingerite, Sodium autinite, Sodium uranospinite, Swartzite, Troegerite, Uranocircite, Uranopilite, Urano-spinite, Zippeite |
| Moderate | Barium uranophane, Meta-ankoleite, Meta-autunite, Meta-uranocircite, Meta-uranopilite, Paraschoepite, Schoepite, Uramphite, Ursilite, Weeksite (var. Gastunite) |
| Weak | Arsenuranospathite, Bayleyite, Bergenite, Billietite, Boltwoodite, Haiweeite, Johannite (var. Peligotite), Metahaiweeite, Metalodevite, Metanovacekite, Metaschoepite, Metazellerite, Metazeunerite, Novacekite, Rabbittite, Sharpite, Strelkinite, Zellerite |

In operation, any fluorescence excited by laser output from laser 12 is collected by the telescope 14 and directed through an appropriate narrow band filter 15 to the photomultiplier tube 16. The primary gain factor in the system is in the photomultiplier tube where there is a typical gain on the order of $10^6$ or 120 db. The buffered fluorescence response pulse is then separated into two paths by similar low pass active filter stages, and further correction for time delays can be obtained by a slight change in the band width of one filter relative to the other, if desired.

With reference also to the Autunite response curve of FIG. 4, the pulse reaches maximum negative value 12 microseconds and decays along the curve 106 after excitation at peak point 104. When this peak occurs, the output from differentiator 52 changes from the negative slope to a positive slope so that differentiator 52 output is zero crossing at the time of the voltage negative peak value. This zero input to comparator 70 is then compared to a grounded input, and the comparator switches logic states to set the flip flop 72 and to command the sample and hold amplifier 34 to hold the peak negative value built up therein. This peak voltage $E_P$ is held until reset on the next laser output pulse and can be fed directly to a voltage measuring device or other dynamic display device which indicates fluorescence intensity. The flip flop 72 also provides a peak timing signal $T_P$ which ends a timing sequence $T_P-T_0$ which is a measure of the fluorescence excitation time $T_R$, the on time of the $T_R$ flip flop 82. The held voltage peak or value $E_P$ is voltage divided by $E_P/e$ (0.368 $E_P$) which feeds one input of comparator 94. The input to the sample and hold amplifier 34 continues to follow the fluorescence decay so that when the peak decays to 0.368 $E_P$, or 50 microseconds after peak 104 in FIG. 4, the two input voltages are equal and the comparator changes logic states indicating the end of the timing sequence $T_e-T_P$, and this constitutes a measure of fluorescence decay time $T_D$ which is the ON time of the $T_D$ flip flop 98.

The foregoing discloses a novel apparatus for surveillance examination of surface outcroppings and the like to determine with greater accuracy the likelihood of presence of uranium ores. The system is particularly effective in ascertaining specific types of secondary uranium ores due to the readout of a greater number of parameters of the fluorescence phenomena. Thus, examination and compilation of the readout data can enable construction of an identifiable signature for nearly all of the oxides of uranium as well as some of the primary ores.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. Apparatus for detection and analysis of uranium minerals deposited in the earth surface, comprising:
   an ultraviolet light source for irradiating the earth surface with ultraviolet light having a first selected wavelength;
   means for detecting fluorescence at a second selected wavelength to provide an electrical output signal indicative thereof;
   first means for analyzing said output signal to generate a voltage indicative of fluorescence peak response;
   second means responsive to said output signal to generate a voltage pulse having a duration equal to fluorescence decay time; and
   third means responsive to said output signal to generate a voltage pulse having a duration equal to fluorescence excitation time.

2. Apparatus as set forth in claim 1 wherein said first means comprises:
   sample and hold amplifier means receiving said output signal;
   differentiator means receiving said output signal to provide a differential signal; and
   comparator means receiving said differential signal to provide a peak time output which triggers the sample and hold amplifier to output said voltage equal to fluorescence peak response.

3. Apparatus as set forth in claim 2 wherein said third means comprises:
   multivibrator means generating an output pulse at excitation time zero; and
   flip flop means receiving said time zero pulse and said peak time output to generate said voltage pulse having a duration equal to fluorescence excitation rise time.

4. Apparatus as set forth in claim 2 wherein said second means comprises:
   voltage divider means receiving input of said voltage indicative of peak response to generate a divided output of selected proportion;
   comparator means receiving input of said divided output and said output signal to generate a voltage indicating time of decay; and
   flip flop means turned off by said time of decay voltage and turned on by said peak time output to generate said voltage pulse having a duration equal to fluorescence decay time.

5. Apparatus as set forth in claim 1 which further includes:
   means for indicating the generated voltage outputs from said first, second and third means.

6. Apparatus as set forth in claim 1 which is further characterized in that:
   said ultraviolet light source is a pulsed laser having a selected wavelength of about 337 nanometers.

7. Apparatus as set forth in claim 1 wherein said means for detecting comprises:
   telescopic means viewing said irradiated earth surface;
   narrow band light filter means disposed in the field of view of said telescopic means; and
   photomultiplier means receiving light from said light filter means for conversion to said electrical output signal.

8. Apparatus as set forth in claim 7 which is further characterized in that:
   said light filter means transmits light within the band of 500 to 550 nanometers.

9. Apparatus as set forth in claim 1 wherein:
   said ultraviolet light source irradiates with light of approximately 337 nanometers; and
   said means for detecting responds to fluorescent light in the band from 500 to 550 nanometers.

* * * * *